US006819844B2

United States Patent
Hunt

(10) Patent No.: US 6,819,844 B2
(45) Date of Patent: Nov. 16, 2004

(54) FIBER-OPTIC BASED SURFACE SPECTROSCOPY

(75) Inventor: Jeffrey H. Hunt, Chatsworth, CA (US)

(73) Assignee: The Boeing Company, Chicago, IL (US)

( * ) Notice: Subject to any disclaimer, the term of this patent is extended or adjusted under 35 U.S.C. 154(b) by 153 days.

(21) Appl. No.: 10/175,986

(22) Filed: Jun. 20, 2002

(65) Prior Publication Data

US 2003/0235381 A1 Dec. 25, 2003

(51) Int. Cl.[7] .................................................. G01J 3/00
(52) U.S. Cl. ........................ 385/122; 356/237; 356/300
(58) Field of Search .......................... 385/122; 356/300, 356/237, 237.1, 237.2, 237.3, 237.4, 335–338, 369, 635–636, 322, 327, 237.5

(56) References Cited

U.S. PATENT DOCUMENTS

| | | | | |
|---|---|---|---|---|
| 4,966,457 A | * | 10/1990 | Hayano et al. | 356/239.7 |
| 5,067,798 A | * | 11/1991 | Tomoyasu | 359/286 |
| 5,108,176 A | * | 4/1992 | Malin et al. | 356/243.1 |
| 5,127,726 A | * | 7/1992 | Moran | 356/237.2 |
| 5,294,289 A | | 3/1994 | Heinz et al. | |
| 5,623,341 A | | 4/1997 | Hunt | |
| 5,712,701 A | * | 1/1998 | Clementi et al. | 356/237.2 |
| 5,715,052 A | * | 2/1998 | Fujino et al. | 356/237.2 |
| 5,875,029 A | | 2/1999 | Jann et al. | |
| 5,883,714 A | | 3/1999 | Jann et al. | |
| 5,898,499 A | | 4/1999 | Pressesky | |
| 5,923,423 A | | 7/1999 | Sawatari et al. | |
| 5,973,778 A | * | 10/1999 | Hunt | 356/300 |
| 6,177,984 B1 | * | 1/2001 | Jacques | 356/39 |
| 6,177,993 B1 | * | 1/2001 | Sommargren | 356/337 |
| 6,317,514 B1 | | 11/2001 | Reinhorn et al. | |
| 6,327,520 B1 | * | 12/2001 | Hooker et al. | 700/259 |
| 6,359,451 B1 | | 3/2002 | Wallmark | |
| 6,563,591 B2 | * | 5/2003 | Maris | 356/496 |
| 6,590,656 B2 | * | 7/2003 | Xu et al. | 356/369 |
| 6,633,831 B2 | * | 10/2003 | Nikoonahad et al. | 702/155 |
| 6,657,736 B1 | * | 12/2003 | Finarov et al. | 356/625 |
| 6,714,300 B1 | * | 3/2004 | Rosencwaig et al. | 356/369 |

OTHER PUBLICATIONS

"Light Waves at the Boundary of Nonlinear Media"—The Physical Review, 128, p. 193, 1962, Bloembergen and P.S. Pershan.

"Surface Studies by Optical Second Harmonic Generation: an Overview"—Journal f Vacuum Science and Technology B, vol. 3, No. 5, Sep. Oct. 1985, pp. 1464–1466, Y.R. Shen.

* cited by examiner

Primary Examiner—Ashok Patel
Assistant Examiner—Dalei Dong
(74) Attorney, Agent, or Firm—Shimokaji & Associates P.C.

(57) ABSTRACT

The system includes a fixed wavelength laser and a tunable wavelength laser as inputs. Respective input optical fibers receive the inputs and transmit them to a first position proximate a location on a surface to be interrogated. Respective fiber coupling optics deliver the inputs to the interrogated location on the surface. The inputs are alignable so that their surface locations of optical illumination overlap on the interrogated location. Output fiber coupling optics receives a reflected output resulting from a three-wave mixing process occurring at the interrogated location. An output optical fiber receives an output of the output fiber coupling optics and transmits the output to a desired position from the interrogated location. An output sensor system receives an output of the output optical fiber and collects, analyzes and interprets the output of the output optical fiber, wherein the fixed wavelength laser, tunable wavelength laser and the output sensor system may be disposed at desired distances and angles from the interrogated location.

36 Claims, 3 Drawing Sheets

FIBER-OPTIC BASED SURFACE SPECTROSCOPY

BACKGROUND OF THE INVENTION

1. Field of the Invention

The present invention relates to monitoring surface conditions and characteristics, such as contamination and corrosion and more particularly to the use of second-order nonlinear optics to perform surface sensitive measurements of these physical and chemical surface parameters with a high degree of specificity.

2. Description of the Related Art

Despite the plethora of surface diagnostics, there is no clear method which has shown superiority over all others. The most evident obstacle to implementation of these diagnostics is the requirement of operation in ultrahigh vacuum environments. The vacuum requirement precipitates from the fact that most surface sensitive analysis techniques involve scattering from the surface at a near-grazing incident angle. The scattering of electrons, x-rays, etc. in this geometry requires that nothing interfere with the input or output on its way to or from the surface. The use of optical interrogation would alleviate this requirement. However, linear optical phenomena are generally bulk phenomena and therefore suffer from a poor ability to discriminate surface characteristics.

In nonlinear optics, outputs are produced at sum, difference or harmonic frequencies of the input(s). Using second order nonlinear optical (NLO) surface spectroscopy to examine the physical properties and behavior of a surface or interface was originally proposed in the 1960's, in "Light Waves at the Boundary of Nonlinear Media" by Bloembergen and P. S. Pershan, The Physical Review, 128, Page 193 (1962). Experimental work involving second harmonic generation was also performed. However, because lasers at the time were comparatively feeble, impractical, slow, etc., there was little subsequent work done on the development of second harmonic generation or, more generally, second order nonlinear optical (NLO) processes at surfaces until considerably later when lasers had evolved sufficiently that their use in an application was simpler.

Recently, researchers have reviewed NLO processing and concluded that lasers had developed enough that they could be used for studying the physical and chemical properties of surfaces and interfaces. For example, a theoretical study of the physics of the interface, and not its engineering aspects, has been performed. See Journal of Vacuum Science and Technology B, Volume 3, Number 5, September October 1985, Pages 1464–1466, Y. R. Shen, "Surface Studies by Optical Second Harmonic Generation: an Overview."

U.S. Pat. No. 5,294,289, T. F. Heinz et al. discuss the use of second harmonic generation as a means to monitor the epitaxial growth of silicon semiconductor structures in a high vacuum chamber. Specifically, they examined the spectroscopic response at the interface between the electronically active silicon and the insulative layer of calcium fluoride. By monitoring the magnitude of the resonance, they could ascertain whether the insulator was present on the surface and whether it had electronically binded to the underlying semiconductor. The optical system that is employed involves the free space propagation of the laser from source to surface and to optical detector. There is no discussion of using optical fibers as the propagation path for inputs or outputs. At the time this patent was granted, optical fibers were not capable of handling high peak power optical pulse formats.

In U.S. Pat. No. 5,623,341, J. H. Hunt discusses the use of sum-frequency generation for the detection of contamination and corrosion on engine parts. In this incarnation, one of the inputs is a tunable IR beam that is tuned to a resonance of the contamination on the surface. The efficiency of the sum-frequency process is increased (so-called resonant enhancement) when the IR beam is resonant with a contaminant. If the contaminant is not present, there is no resonant enhancement. By comparing on and off resonant signals, the presence and level of contaminant can be deduced. The optical system that is employed involves the free space propagation of the laser from source to surface and to optical detector. There is no discussion of using optical fibers as the propagation path for inputs or outputs.

In U.S. Pat. No. 5,875,029, P. C. Jann et al. describe a versatile optical inspection instrument and method to inspect magnetic disk surfaces for surface defects. The device provides surface position information of the defects. However, the technique involves only linear optical processes. That is, the input and output light wavelengths are the same. There is also no discussion of optical fiber implementation.

In U.S. Pat. No. 5,883,714, Jann et al. describe a versatile optical inspection instrument and method to inspect magnetic disk surfaces for surface defects. The device is based on interferometric measurement and detects contaminants by measuring the Doppler shift in the light that results from scanning the light onto a contaminant or defect. By scanning, the device provides surface position information of the defects. However, the technique involves only linear optical processes and senses only phase changes. That is, the input and output light wavelengths are the same and there is no discussion of the use of optical fibers.

In U.S. Pat. No. 5,898,499, J. L. Pressesky discusses a system for detecting local surface discontinuities in magnetic storage discs. The device is an interferometric detector which scans the disc in a spiral motion. Local defects cause local changes in phase which are measured by interferometric techniques. This is a linear optical technique.

In U.S. Pat. No. 5,932,423, T. Sawatari et al. discuss a scatterometer for detecting surface defects in semiconductor wafers. This device is a linear interferometric device.

In U.S. Pat. No. 5,973,778, J. H. Hunt discusses the use of second harmonic generation for investigating molecular alignment within a thin polyimide film. The technique uses changes in the second harmonic polarization to determine surface molecular alignment. There is no discussion of the use of optical fibers as a propagation path for inputs or outputs. The nonlinear optical response of a semiconductor will be quite different than that of a liquid crystal film.

In U.S. Pat. No. 6,317,514 B1, S. Reinhorn et al. discuss a method and apparatus for inspecting a wafer surface to detect the presence of conductive material on the wafer. The device uses UV initiated electron emission to determine the location of conductive areas. Those areas which are metal will emit electrons. If the area, which is supposed to be conductive, is not, there will be no electron emission.

In U.S. Pat. No. 6,359,451 B1, G. N. Wallmark discusses a system for testing for opens and shorts between conductor traces on a circuit board. The technique uses electron scattering to perform its diagnostics and has no optics associated with it.

SUMMARY

The present invention is a fiber-based nonlinear optical system for performing surface-sensitive spectroscopic characterizations on a surface to be interrogated. A first optical source provides a first input, the first optical source comprising a fixed wavelength laser. A first input optical fiber receives the first input and transmits the first input to a first position proximate a location on a surface to be interrogated. The first input fiber coupling optics receives the first input from an output end of the first input optical fiber and delivers the first input to the interrogated location on the surface. A second optical source provides a second input. The second optical source comprises a tunable wavelength laser. A second input optical fiber receives the second input and transmits the second input to a second position proximate the interrogated location. A second input fiber coupling optics receives the second input from an output end of the second input optical fiber and delivers the second input to the interrogated location on the surface. The first and second inputs are alignable so that their surface locations of optical illumination overlap on the interrogated location. Output fiber coupling optics receives a reflected output resulting from a three-wave mixing process occurring at the interrogated location. An output optical fiber receives an output of the output fiber coupling optics and transmits the output to a desired third position from the interrogated location. An output sensor system receives an output of the output optical fiber and collects, analyzes and interprets the output of the output optical fiber, wherein the first and second optical sources and the output sensor system may be disposed at desired distances and angles from the interrogated location.

When implementing an optical diagnostic, the laser and detector are often objects which are large or cumbersome or whose operation would benefit from remote location from the sample. If the laser or detector is located remotely, the optical inputs or outputs must be propagated to and from the surface via a series of mirrors, lenses and other optics. A line of sight must be maintained between source and surface and surface and detector, often causing inconvenience and increasing the complexity of implementation.

If, instead, one uses fiber optics, the propagation issues become simpler since the optical fiber can follow an arbitrary path to and from the surface. Optical fibers have recently become able to propagate high peak power pulses. Previously, attempts to do so would result in damage to the fiber.

Other objects, advantages, and novel features will become apparent from the following detailed description of the invention when considered in conjunction with the accompanying drawings.

DETAILED DESCRIPTION OF THE INVENTION

Figure 1:
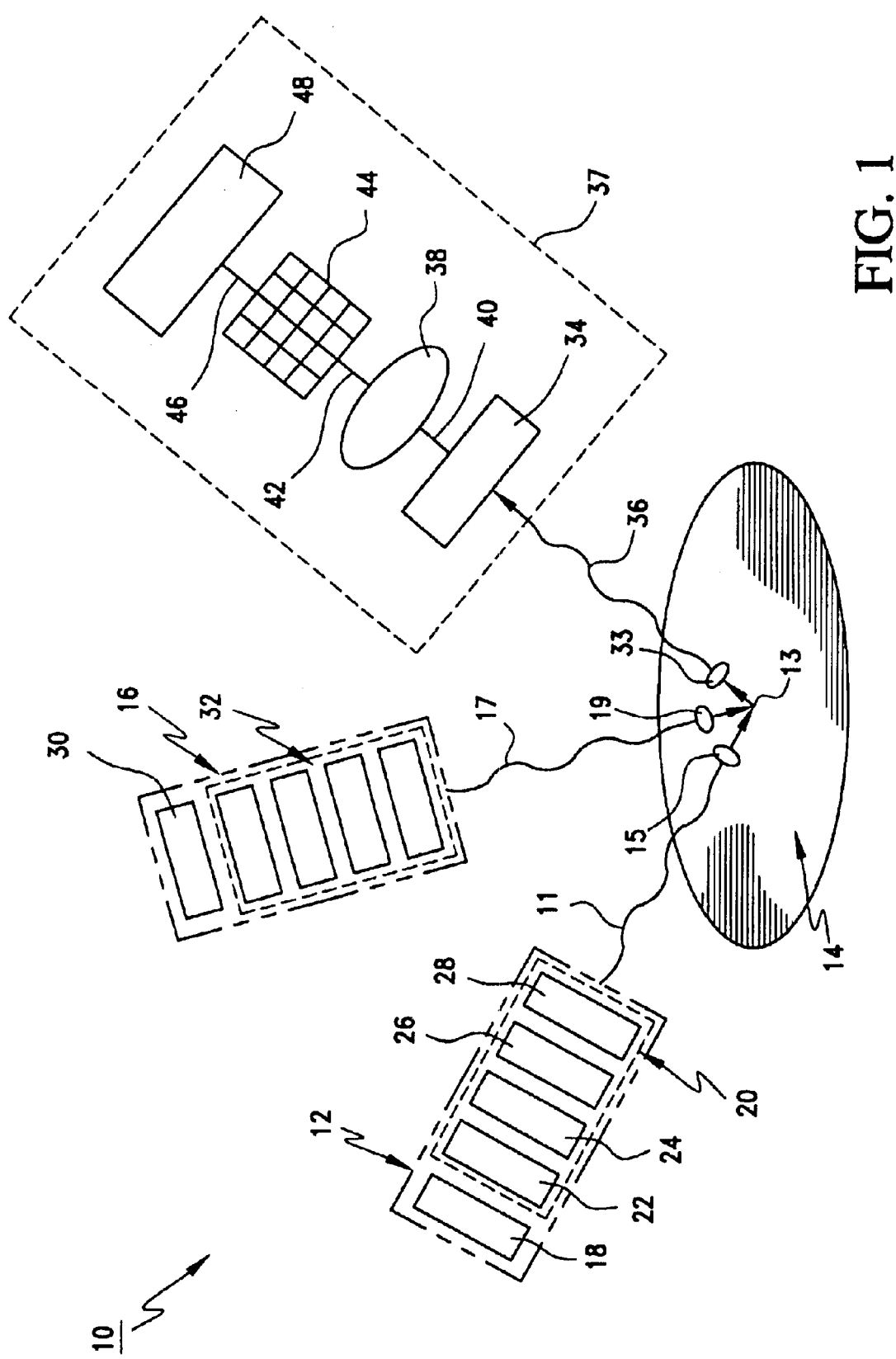
FIG. 1 is a schematic representation of the fiber-based nonlinear optical system of the present invention.

Referring now to the drawings and the characters of reference marked thereon, FIG. 1 illustrates a preferred embodiment of the nonlinear optical system of the present invention, designated generally as 10. Fiber-based nonlinear optical system 10 includes a first optical source, indicated by phantom lines 12 for providing a first input. A first input optical fiber 11 receives the first input and transmits that first input to a first position proximate a location 13 on a surface 14 to be interrogated. First input fiber coupling optics 15 receives the first input from an output end of the first input optical fiber 11 and delivers the first input to the interrogated location on the surface 14.

A second optical source 16 provides a second input that is also eventually directed to the location 13 on the surface 14 to be interrogated. A second input optical fiber 17 receives the second input and transmits that second input to a second position also proximate the location 13 on the surface 14 to be interrogated. Second input fiber coupling optics 19 receives the second input from an output end of the second input optical fiber 17 and delivers the second input to the interrogated location on the surface 14.

The first and second inputs are aligned when output from their respective coupling optics 15, 19 so that their surface areas of optical illumination overlap on the interrogated surface 14. This alignment may be implemented via a series of refractive and reflective elements. For example, by changing their tilt in two axes, two mirrors in series can propagate a laser beam to any position on a surface.

The first optical source 12 includes a fixed wavelength laser 18 in optical communication with an associated input optics 20. The input 18 is preferably a solid state laser or a diode laser. It may be, for example a pulsed diode laser, a continuous-wave diode laser, a pulsed solid state laser, a continuous-wave solid state laser, a flash-lamp pumped solid state laser, or a diode pumped solid state laser.

The input optics 20 preferably includes an input polarizer 22, an input wavelength discriminator 24, an input spatial filter 26 and an input propagation optics 28. The input polarizer 22 could be, for example, a brewster angle polarizer, a thin film polarizer, a Glan-air or Glan-Thompson polarizer or other crystal polarizer. The wavelength discriminator 24 may be, for example, a color filter, a dielectric film, a holographic transmission filter, or a grating. The input propagation optics 20 could be formed of one or more refractive or reflective optics which, when used in combination, control the divergence or convergence of the beam as it propagates towards the first input optical fiber 11.

The second optical source 16 includes a tunable laser 30 and associated input optics 32. The input optics 32 may be as described above with respect to the first optical source 12. However, the optics 32 is optimized for the wavelength of the second optical source 16. The input 30 is preferably a tunable visible laser and may be, for example, a tunable optical parametric oscillator (pulsed or continuous-wave).

Output fiber coupling optics 33 receives a reflected output resulting from a three-wave mixing process occurring at the interrogated location. The three-wave mixing process may comprise sum-frequency generation or difference-frequency generation, as discussed in more detail below.

An output optical fiber 36 receives an output of the output fiber coupling optics 33 and transmits the output to a desired third position from the interrogated location 13.

An output sensor system 37 receives the output of the output optical fiber 36 and collects, analyzes and interprets the output of the output optical fiber 36. Thus, the first and second optical sources 12,16, and also the output sensor system 37, may be disposed at desired distances and angles from the interrogated location 13.

An output wavelength discriminator 34 of the output sensor system 37 receives the reflected output generated on the interrogated location 13. The output wavelength discriminator 34 is substantially non-transmissive at desired frequencies and substantially transmissive at other desired frequencies in accordance with the specific three-wave mixing process being used. The output wavelength discriminator 34, like the input wavelength discriminators, may comprise a color filter, a dielectric film, a holographic transmission filter, or a grating.

Signal collection optics 38 receives the three-wave mixing output 40 of the output wavelength discriminator 34 and directs the propagation of the output so that a collected optical light signal 42 is formed after propagation through the signal collection optics 38. The signal collection optics 38 may be either refractive or reflective optics which, when used in conjunction, act to control the divergence of the light coming from the surface so that as much of the light signal, as is technically possible, is collected for subsequent analysis.

An optical detector 44 converts the collected optical light signal 42 to an electronic signal 46, thus monitoring the intensity of the three-wave mixing output wavelength, as a function of surface properties. The optical detector 44 may be, for example, an avalanche photodiode, which creates an electronic signal proportional to the amount of light incident on it.

An electronic signal analyzer 48 analyzes the electronic signal 46 for providing surface-sensitive spectroscopic characterizations. The electronic signal analyzer 48 may be, for example, a computer with suitable internal electronics to implement the appropriate mathematical algorithms to interpret the signals.

Figure 2A:
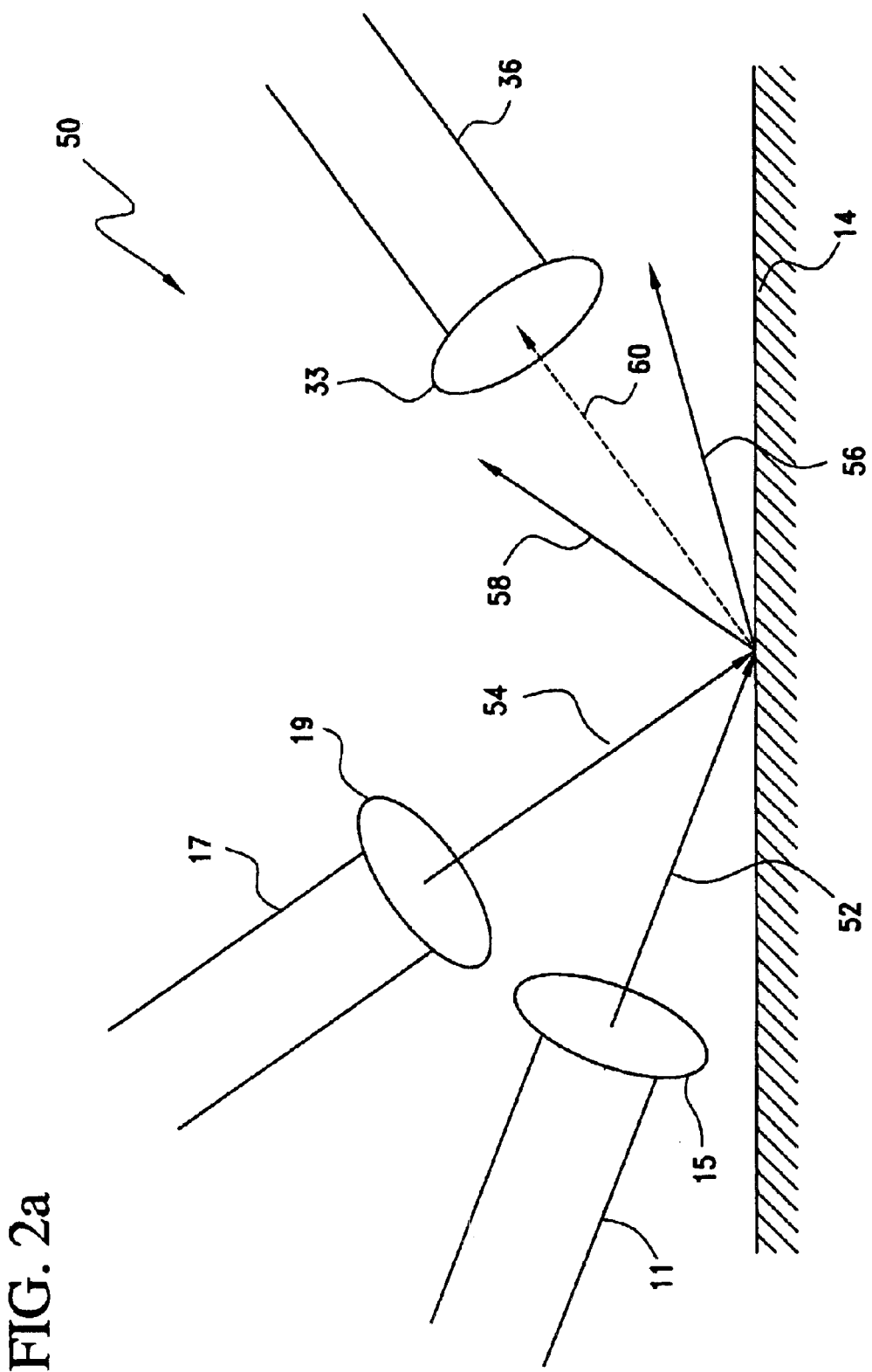
FIG. 2a is an enlarged schematic representation of the portion of the optical system proximate the surface illustrating the use of sum-frequency generation.

Referring now to FIG. 2a a schematic representation is illustrated, designated generally as 50 in which the input optical fibers 11, 17 with their associated coupling optics 15, 19 and the output fiber 36 with its coupling optics 33 are configured for sum-frequency generation. In this process the wavelength discriminator is substantially transmissive at the sum-frequency and substantially non-transmissive at frequencies lower than the sum-frequency. The first laser input 52 and second laser input 54 provide respective reflections, designated 56, 58. The sum-frequency output 60 propagation direction lies between reflections 56 and 58. The output fiber coupling optics 33 should therefore be positioned between the two reflections 56, 58.

Figure 2B:
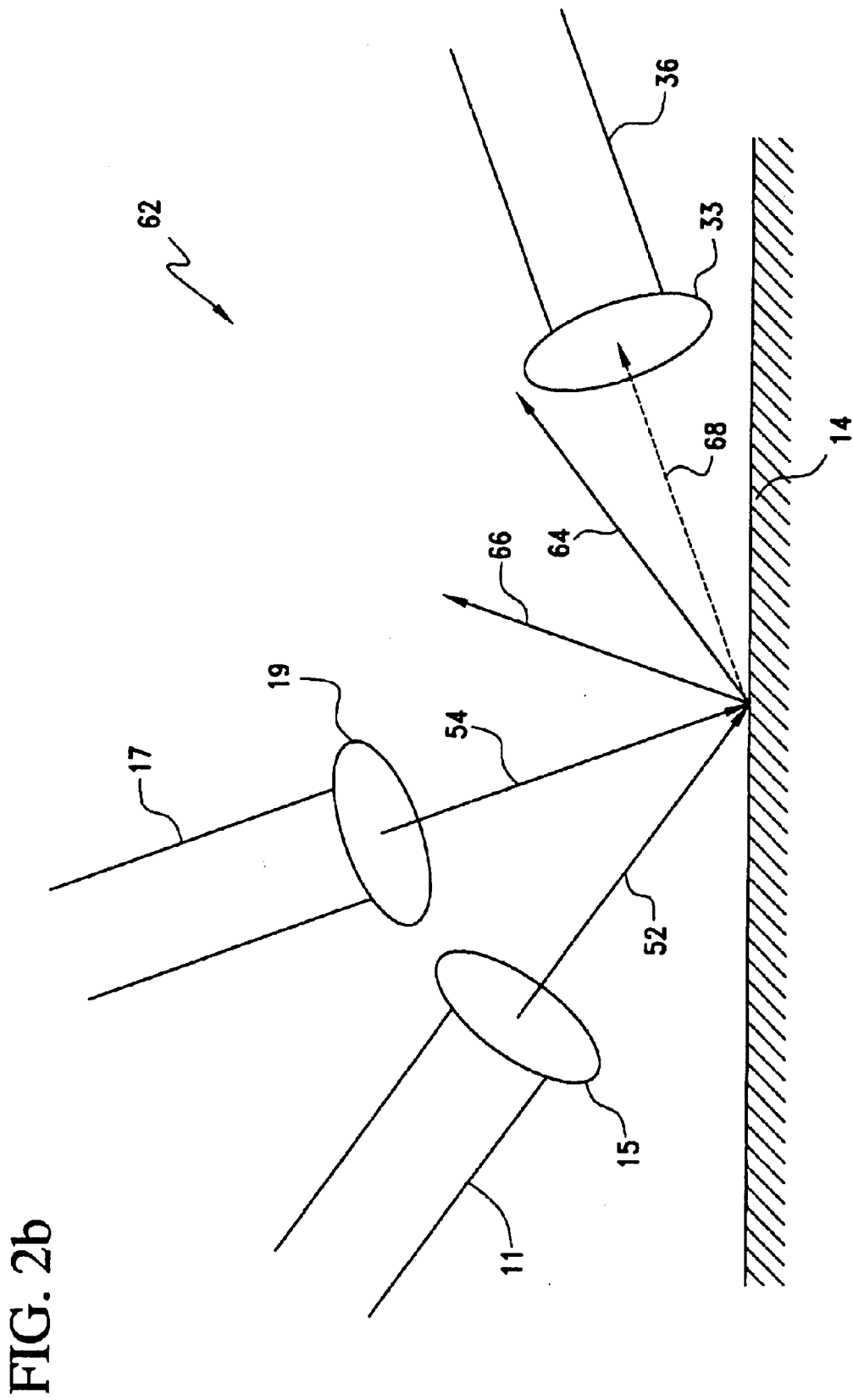
FIG. 2b is an enlarged schematic representation of the portion of the optical system proximate the surface illustrating the use of difference-frequency generation.

Referring now to FIG. 2b a schematic representation is illustrated, designated generally as 62, in which the input optical fibers 11, 17 with their associated coupling optics 15, 19 and the output fiber 36 with its coupling optics 33 are configured for difference-frequency generation. In this process the wavelength discriminator is substantially transmissive at the difference-frequency and substantially non-transmissive at frequencies higher than the difference-frequency. The first laser input 52 and second laser input 54 provide respective reflections, designated 64, 66. The sum-frequency output 68 propagation direction lies below reflections 64 and 66. The output fiber coupling optics 33 should therefore be positioned below the two reflections 64, 66.

In a preferred embodiment the first optical source may comprise a Nd:YAG laser operating on the 1.064 micron line or a Nd:YAG laser and a harmonic converter for operation at the second or third harmonic of the laser fundamental output wavelength. The Nd:YAG laser may be a diode pumped or flashlamp pumped source. The operation of the Nd:YAG may be continuous-wave or it may be pulsed. If it is pulsed, it may operate with a maximum pulse length of 10 nanoseconds. The optimal pulse length is less than 1 picosecond.

The input optics of the first optical source preferably includes a steering apparatus, comprising two mirrors aligned so that that their surface normals are non-coplanar. It also preferably includes a polarization rotator comprising a half-wave plate. The half-wave plate should be optimized for an output wavelength of the input laser. The input optics also preferably uses a linear polarizer that is aligned so that an output wavelength is p or s polarized with the polarization referenced to the surface to be interrogated. A spot shaping apparatus is used, comprising a series of lenses, for creating a controlled spot size on the surface to be interrogated. Finally, a narrow band optical filter is used that passes only an output wavelength or harmonic wavelength of the input laser.

In this preferred embodiment, the second optical source preferably comprises a tunable optical parametric oscillator and amplifier. The optical parametric oscillator and amplifier may be continuous-wave operation. The optical parametric oscillator and amplifier may be pulsed operation. If pulsed operation is used, the pulse may have a maximum pulse duration of 10 nanoseconds and an optimum pulse duration of less than 1 picosecond. A steering apparatus is utilized including two mirrors aligned so that that their surface normals are non-coplanar, with the mirrors' reflectances being optimized for a desired output wavelength of the laser. A polarization rotator is used that is operative in the desired range. A linear polarizer is used and is aligned so that an output wavelength is p or s polarized with the polarization referenced to the surface to be interrogated. Finally, a spot shaping apparatus is used, including a series of lenses for creating a controlled spot size on the surface to be interrogated.

The output wavelength discriminator preferably includes an iris; a filter in optical communication with the iris for passing the sum frequency wavelength; and, a linear polarizer in optical communication with the filter, aligned to detect either the p or s polarized sum-frequency wavelength, wherein the polarization is referenced to the surface where the sum-frequency light is generated.

The signal collection optics preferably includes a telescope system comprising a plurality of telescope system lenses having coatings optimized for the sum-frequency or difference-frequency, depending on the application. The optical detector preferably comprises a semiconductor detector being electronically gated to only detect output light generated by the input laser pulses. A computer collects and analyzes the electronic data from the optical detector.

There are many possible applications for the fiber-based nonlinear optical system of the present invention. The optical system can be used, for example, as an in-situ surface monitor for manufacturing. It can used to detect small amounts of surface contamination, both in particulate form and as chemical residue. Corrosion can be sensed at its onset. Thin films, such as those associated with liquid crystals or optical coatings, can be monitored for chemical composition and molecular alignment. In fact, most any surface whose physical or chemical properties require diagnostic measurement can employ the present optical system.

Obviously, many modifications and variations of the present invention are possible in light of the above teachings. It is, therefore, to be understood that within the scope of the appended claims, the invention may be practiced otherwise than as specifically described.

What is claimed and desired to be secured by Letters Patent of the United States is:

1. A fiber-based nonlinear optical system for performing surface-sensitive spectroscopic characterizations on a surface to be interrogated, comprising:

a) a first optical source for providing a first input, said first optical source comprising a fixed wavelength laser;

b) a first input optical fiber for receiving said first input and transmitting said first input to a first position proximate a location on a surface to be interrogated;

c) first input fiber coupling optics for receiving said first input from an output end of said first input optical fiber and delivering said first input to the interrogated location on the surface;

d) a second optical source for providing a second input, said second optical source comprising a tunable wavelength laser;

e) a second input optical fiber for receiving said second input and transmitting said second input to a second position proximate the interrogated location;

f) second input fiber coupling optics for receiving said second input from an output end of said second input optical fiber and delivering said second input to the interrogated location on the surface, said first and second inputs being aligned so that their surface locations of optical illumination overlap on said interrogated location;

g) output fiber coupling optics for receiving a reflected output resulting from a nonlinear three-wave mixing process of said first and second inputs being aligned so that their surface locations of optical illumination overlap on said interrogated location, said nonlinear three-wave mixing process comprising sum-frequency generation end difference frequency generation occurring at said interrogated location, wherein:

said output fiber coupling optics are positioned between the reflection of said first input from the surface and the reflection of said second input from the surface for a sum-frequency output propagation direction and said output fiber coupling optics are positioned below both the reflection of said first input from the surface and the reflection of said second input from the surface for a difference-frequency output propagation direction;

h) an output optical fiber for receiving an output of said output fiber coupling optics and transmitting the output to a desired third position from said interrogated location; and i) an output sensor system for receiving an output of said output optical fiber and collecting, analyzing and interpreting said output of said output optical fiber, wherein said first and second optical sources end said output sensor system may be disposed at desired distances and angles from said interrogated location.

2. The fiber-based nonlinear optical system of claim 1, wherein said output sensor system comprises an output wavelength discriminator for receiving the reflected output, said output wavelength discriminator being substantially non-transmissive at desired frequencies and substantially transmissive at other desired frequencies.

3. The fiber-based nonlinear optical system of claim 1, wherein said output sensor system, comprises:

a) an output wavelength discriminator for receiving the reflected output, said output wavelength discriminator being substantially non-transmissive at desired frequencies and substantially transmissive at other desired frequencies; and b) signal collection optics for receiving an output of said output wavelength discriminator and directing the propagation of said output of the output wavelength discriminator so that a collected optical light signal is formed after propagation through said signal collection optics.

4. The fiber-based nonlinear optical system of claim 1, wherein said output sensor system, comprises:

a) an output wavelength discriminator for receiving the reflected output, said output wavelength discriminator being substantially non-transmissive at desired frequencies and substantially transmissive at other desired frequencies;

b) signal collection optics for receiving an output of said output wavelength discriminator and directing the propagation of said output of the output wavelength discriminator so that a collected optical light signal is formed after propagation through said signal collection optics; and c) an optical detector for converting said collected optical light signal to an electronic signal, thus monitoring the intensity of a three-wave mixing output wavelength of the reflected output for providing surface-sensitive spectroscopic characterizations on the surface to be interrogated.

5. The fiber-based nonlinear optical system of claim 1, wherein said output sensor system, comprises:

a) an output wavelength discriminator for receiving the reflected output, said output wavelength discriminator being substantially non-transmissive at desired frequencies and substantially transmissive at other desired frequencies;

b) signal collection optics for receiving an output of said output wavelength discriminator and directing the propagation of said output of the output wavelength discriminator so that a collected optical light signal is formed after propagation through said signal collection optics;

c) an optical detector for converting said collected optical light signal to an electronic signal, thus monitoring the intensity of a three-wave mixing output wavelength or the reflected output for providing surface-sensitive spectroscopic characterizations on the surface to be interrogated; and d) an electronic signal analyzer for analyzing said electronic signal for providing the surface-sensitive spectroscopic characterizations.

6. The fiber-based nonlinear optical system of claim 1, wherein said three-wave mixing process comprises sum-frequency generation.

7. The fiber-based nonlinear optical system of claim 1, wherein said three-wave mixing process comprises sum-frequency generation and said output sensor system comprises an output wavelength discriminator for receiving the reflected output, said output wavelength discriminator being substantially transmissive at the sum-frequency and substantially non-transmissive at frequencies lower than the sum-frequency.

8. The fiber-based nonlinear optical system at claim 1, wherein said three-wave mixing process comprises sum-frequency generation end said output sensor system comprises:

a) an output wavelength discriminator for receiving the reflected output, said output wavelength discriminator being substantially transmissive at the sum-frequency and substantially non-transmissive at frequencies lower than the sum-frequency;

b) signal collection optics for receiving an output of said output wavelength discriminator and directing the propagation of said output of the output wavelength discriminator so that a collected optical light signal is formed after propagation through said signal collection optics; and c) an optical detector for converting said collected optical light signal to an electronic signal, thus monitoring the intensity of the sum-frequency wavelength for providing surface-sensitive spectroscopic characterizations on the surface to be interrogated.

9. The fiber-based nonlinear optical system of claim 1, wherein said three-wave mixing process comprises sum-frequency generation and said output sensor system comprises:

a) an output wavelength discriminator for receiving the reflected output, said output wavelength discriminator being substantially transmissive at the sum-frequency and substantially non-transmissive at frequencies lower than the sum-frequency;

b) signal collection optics for receiving an output of said output wavelength discriminator and directing the propagation of said output of the output wavelength discriminator so that a collected optical light signal is formed after propagation through said signal collection optics;

c) an optical detector for converting said collected optical light signal to an electronic signal, thus monitoring the intensity of the sum-frequency wavelength for providing surface-sensitive spectroscopic characterizations on the surface to be interrogated; and d) an electronic signal analyzer for analyzing said electronic signal for providing the surface-sensitive spectroscopic characterizations.

10. The fiber-based nonlinear optical system of claim 1, wherein said three-wave mixing process comprises difference-frequency generation.

11. The fiber-based nonlinear optical system of claim 1, wherein said three-wave mixing process comprises difference-frequency generation end said output sensor system comprises an output wavelength discriminator for receiving the reflected difference-frequency generated on said interrogated location, said output wavelength discriminator being substantially transmissive at the difference-frequency, but being substantially non-transmissive at frequencies higher than the difference-frequency.

12. The fiber-based nonlinear optical system of claim 1, wherein said three-wave mixing process comprises difference-frequency generation and said output sensor system comprises:

a) an output wavelength discriminator for receiving the reflected difference-frequency generated on said interrogated location, said output wavelength discriminator being substantially transmissive at the difference-frequency, but being substantially non-transmissive at frequencies higher than the difference-frequency;

b) signal collection optics for receiving an output of said output wavelength discriminator and directing the propagation of said output of the output wavelength discriminator so that a collected optical light signal is formed after propagation through said signal collection optics; and c) an optical detector for converting said collected optical light signal to an electronic signal, thus monitoring the intensity of the sum-frequency wavelength for providing surface-sensitive spectroscopic characterizations on the surface to be interrogated.

13. The fiber-based nonlinear optical system of claim 1, wherein said three-wave mixing process comprises difference-frequency generation and said output sensor system comprises:

a) an output wavelength discriminator for receiving the reflected difference-frequency generated on said interrogated location, said output wavelength discriminator being substantially transmissive at the difference-frequency, but being substantially non-transmissive at frequencies higher than the difference-frequency;

b) signal collection optics for receiving an output of said output wavelength discriminator and directing the propagation of said output of the output wavelength discriminator so that a collected optical light signal is formed after propagation through said signal collection optics;

c) an optical detector for converting said collected optical light signal to an electronic signal, thus monitoring the intensity of the sum-frequency wavelength for providing surface-sensitive spectroscopic characterizations on the surface to be interrogated; and d) an electronic signal analyzer for analyzing said electronic signal for providing the surface-sensitive spectroscopic characterizations.

14. The fiber-based nonlinear optical system of claim 1, wherein said first optical source comprises said fixed wavelength laser in optical communication with a first input optics.

15. The fiber-based nonlinear optical system of claim 1, wherein said first optical source comprises said fixed wavelength laser in optical communication with a first input optics, said first input optics comprising a first input polarizer, a first input wavelength discriminator, a first input spatial filter and first input propagation optics in optical communication.

16. The fiber-based nonlinear optical system of claim 1, wherein said second optical source comprises said tunable wavelength laser in optical communication with a second input optics.

17. The fiber-based nonlinear optical system of claim 1, wherein said second optical source comprises said tunable laser in optical communication with a second input optics, said second input optics comprising a second input polarizer, a second input wavelength discriminator, a second input spatial filter and second input propagation optics in optical communication.

18. The fiber-based nonlinear optical system of claim 1, wherein said first optical source comprises a flash-lamp pumped solid state laser.

19. The fiber-based nonlinear optical system of claim 1, wherein said first optical source comprises a diode pumped solid state laser.

20. The fiber-based nonlinear optical system of claim 1, wherein said first optical source comprises a Nd:YAG laser operating on the 1.064 micron line.

21. The fiber-based nonlinear optical system of claim 1, wherein said first optical source comprises a flash-lamp pumped Nd:YAG laser operating on the 1.064 micron line.

22. The fiber-based nonlinear optical system of claim 1, wherein said first optical source comprises a diode pumped Nd:YAG laser operating on the 1.064 micron line.

23. The fiber-based nonlinear optical system of claim 1, wherein said first optical source comprises a pulsed Nd:YAG laser operating on the 1.064 micron line.

24. The fiber-based nonlinear optical system of claim 1, wherein said first optical source comprises a continuous-wave Nd:YAG laser operating on the 1.064 micron line.

25. The fiber-based nonlinear optical system of claim 1, wherein said first optical source comprises a Nd:YAG laser and a harmonic converter for operation at the second or third harmonic of the laser fundamental output wavelength.

26. The fiber-based nonlinear optical system of claim 1, wherein said first optical source comprises a Nd:YAG laser operating on the 1.064 micron line and a maximum pulse length of 10 nanoseconds.

27. The fiber-based nonlinear optical system of claim 1, wherein said first optical source comprises a Nd:YAG laser operating on the 1.064 micron line and a pulse length of less then 1 picosecond.

28. The fiber-based nonlinear optical system of claim 1, wherein said second optical source comprises a tunable optical parametric oscillator.

29. The fiber-based nonlinear optical system of claim 1, wherein said second optical source comprises a pulsed laser.

30. The fiber-based nonlinear optical system of claim 1, wherein said second optical source comprises a continuous-wave laser.

31. The fiber-based nonlinear optical system of claim 1, wherein said second optical source comprises a Nd:YAG laser operating on the 1.064 micron line and a maximum pulse length of 10 nanoseconds.

32. The fiber-based nonlinear optical system of claim 1, wherein said second optical source comprises a Nd:YAG laser operating on the 1.064 micron line and a pulse length of less than 1 picosecond.

33. A method for performing surface-sensitive spectroscopic characterizations on a surface to be interrogated, comprising:
  a) directing a first input from a first optical source, through a first input optical fiber and to a first position proximate a location on a surface to be interrogated, said first input comprising a fixed wavelength laser;
  b) utilizing first input fiber coupling optics for receiving said first input from an output end of said first input optical fiber and delivering said first input to the interrogated location on the surface;
  c) directing a second input from a second optical source, through a second input optical fiber to a second position proximate the interrogated location, second input comprising a tunable wavelength laser, said first and second inputs being aligned so that their surface locations of optical illumination overlap on said interrogated location;
  d) receiving, via output fiber coupling optics, a reflected output resulting from a nonlinear three-wave mixing process of said first and second inputs being aligned so that their surface locations of optical illumination overlap on said interrogated location, said nonlinear three-wave mixing process comprising sum-frequency generation and difference frequency generation occurring at said interrogated location, further including:
    positioning said output fiber coupling optics between the reflection of said first input from the surface and the reflection of said second input from the surface for a sum-frequency output propagation direction and positioning said output fiber coupling optics below both the reflection of said first input from the surface and the reflection of said second input from the surface for a difference-frequency output propagation direction:
  e) receiving an output of said output fiber coupling optics, via an output optical fiber, and transmitting the output to a desired third position from said interrogated location; and
  f) receiving an output of said output optical fiber end collecting, analyzing and interpreting said output of said output optical fiber, wherein said first and second optical sources and said output sensor system may be disposed at desired distances and angles from said interrogated location.

34. The method of claim 33, wherein said three-wave mixing process comprises sum-frequency generation.

35. The method of claim 33, wherein said three-wave mixing process comprises difference-frequency generation.

36. A fiber-based nonlinear optical system for performing surface-sensitive spectroscopic characterizations on a surface to be interrogated, comprising:
  a) a first optical source for providing a first input, said first optical source comprising a fixed wavelength laser;
  b) a first input optical fiber for receiving said first input and transmitting said first input to a first position proximate a location on a surface to be interrogated;
  c) first input fiber coupling optics for receiving said first input from an output end of said first input optical fiber and delivering said first input to the interrogated location on the surface;
  d) a second optical source for providing a second input, said second optical source comprising a tunable wavelength laser;
  e) a second input optical fiber for receiving said second input and transmitting said second input to a second position proximate the interrogated location;
  f) second input fiber coupling optics for receiving said second input from an output end of said second input optical fiber and delivering said second input to the interrogated location on the surface, said first and second inputs being aligned so that their surface locations of optical illumination overlap on said interrogated location;
  g) output fiber coupling optics for receiving a reflected output resulting from a nonlinear three-wave mixing process of said first and second inputs being aligned so that their surface locations of optical illumination overlap on said interrogated location, occurring at said interrogated location, said nonlinear three-wave mixing process comprising difference-frequency generation, wherein:
    said output fiber coupling optics are positioned below both the reflection of said first input from the surface and the reflection of said second input from the surface for a difference-frequency output propagation direction:
  h) an output optical fiber for receiving an output of said output fiber coupling optics and transmitting the output to a desired third position from said interrogated location; and
  i) an output sensor system for receiving an output of said output optical fiber and collecting, analyzing and interpreting said output of said output optical fiber, wherein said first and second optical sources and said output sensor system may be disposed at desired distances and angles from said interrogated location.

* * * * *